(12) United States Patent
Baldo et al.

(10) Patent No.: US 8,154,729 B2
(45) Date of Patent: Apr. 10, 2012

(54) NEAR FIELD DETECTOR FOR INTEGRATED SURFACE PLASMON RESONANCE BIOSENSOR APPLICATIONS

(75) Inventors: Marc A Baldo, Lexington, MA (US); Mihail Bora, Livermore, CA (US); Jonathan K Mapel, Boston, MA (US); Kemal Celebi, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/774,974

(22) Filed: May 6, 2010

(65) Prior Publication Data

US 2010/0328671 A1 Dec. 30, 2010

Related U.S. Application Data

(63) Continuation of application No. PCT/US2008/084843, filed on Nov. 26, 2008.

(60) Provisional application No. 60/990,428, filed on Nov. 27, 2007.

(51) Int. Cl.
*G01N 21/55* (2006.01)

(52) U.S. Cl. ...................... 356/445; 356/311

(58) Field of Classification Search .................. 356/317, 356/445, 311, 300, 417, 948, 949; 250/483.1, 250/487.1, 488.1, 486.1, 458.1, 459.1, 461.2, 250/465.1, 466.1; 436/171, 172, 518, 519, 436/524, 164, 805, 807; 435/287.1, 287.9, 435/288.7; 385/129, 131
See application file for complete search history.

(56) References Cited

U.S. PATENT DOCUMENTS

| 5,196,702 A | 3/1993 | Tsuji et al. |
| 5,841,143 A * | 11/1998 | Tuma et al. ................. 250/458.1 |
| 7,297,966 B2 * | 11/2007 | Wei et al. .................... 250/492.2 |
| 2005/0269578 A1 * | 12/2005 | Barnes et al. .................. 257/81 |
| 2007/0164377 A1 * | 7/2007 | Gruhlke et al. ............... 257/414 |

* cited by examiner

*Primary Examiner* — Tri T Ton
(74) *Attorney, Agent, or Firm* — Gesmer Updegrove LLP

(57) ABSTRACT

A near-field surface plasmon detector is provided. The near-field surface plasmon detector includes one or more semiconductor layers that absorb one or more surface plasmons of thin metal films in the vicinity of the semiconductor layer. The surface plasmons are excited by incoming light being emitted from a light emitting source. The metal films are also employed as electrical contacts used to capture photocurrent generated after absorption of surface plasmons by the semiconductor layers.

22 Claims, 5 Drawing Sheets

NEAR FIELD DETECTOR FOR INTEGRATED SURFACE PLASMON RESONANCE BIOSENSOR APPLICATIONS

PRIORITY INFORMATION

This application is a continuation of International Application No. PCT/US2008/84843, filed on Nov 26, 2008 which claims priority to U.S. Provisional Application No. 60/990,428 filed Nov 27, 2007, both of which are incorporated herein by reference in their entireties.

GOVERNMENTAL SPONSORSHIP INFORMATION

This invention was made with government support under Grant Nos. DAAD19-02-D-0002 and W911NF-07-D-0004, awarded by the Army Research Office. The government has certain rights in this invention

BACKGROUND OF THE INVENTION

The invention is related to the field of biosensors, and in particular to an integrated surface plasmon resonance biosensor.

Despite widespread demand there remains an unmet need for cost effective biosensors. Applications in research laboratories, home and point of care diagnostics, process industries, environmental monitoring, security and bio-defense, require the measurement of bio-analytes with high specificity and minimal time lag between sample collection and measurement readout. Among commonly used sensing methods, surface plasmon resonance (SPR) achieves relatively high sensitivity (0.5 ng/cm$^2$), and provides the benefits of label free detection and real time measurement of binding kinetics, while integration with microfluidics reduces the sample size and enables high throughput. SPR biosensors are highly versatile tools, being routinely used to examine protein-protein, antibody-antigen, and receptor-ligand interactions. However, they are also large, difficult to transport and relatively costly, due to their dependence on precise calibration and alignment of the internal optics.

SUMMARY OF 1HE INVENTION

According to one aspect of the invention, there is provided a near-field surface plasmon detector. The near-field surface plasmon detector includes a semiconductor structure that measures one or more surface plasmons of a sample being tested using incoming light being emitted from a light emitting source. One or more electrodes are positioned on or near the semiconductor structure. The one or more electrodes include one or more electrical contacts used to output electrical power under operation.

According to another aspect of the invention, there is provided a method of forming a near-field surface plasmon detector. The method includes providing a semiconductor structure that measures one or more surface plasmons of a sample being tested using incoming light being emitted from a light emitting source. Moreover, the method includes positioning one or more electrodes on or near the semiconductor structure. The one or more electrodes include one or more electrical contacts used to output electrical power under operation.

DETAILED DESCRIPTION OF THE INVENTION

The invention describes an integrated surface plasmon resonance biosensor to enable compact and portable biosensing at high sensitivities. To replace the far field detector traditionally used to detect surface plasmons, one can integrate a near field detector below a functionalized a film comprising layers of gold and silver or the like. The evanescent field of a surface plasmon at an aqueous-gold interface is converted into photocurrent by a thin film organic heterojunction diode.

The inventive near field detector is equivalent to the traditional far field measurement of reflectivity. The sensor is stable and reversible in an aqueous environment for extended periods. For specific binding of neutravidin, the sensitivity is three times lower than a comparable conventional SPR biosensor. The sensitivity of the near field detector can be further improved by reducing surface roughness of the layers used and optimization of the device design, especially the substitution of silver for gold in some of the electrodes.

Figure 1:
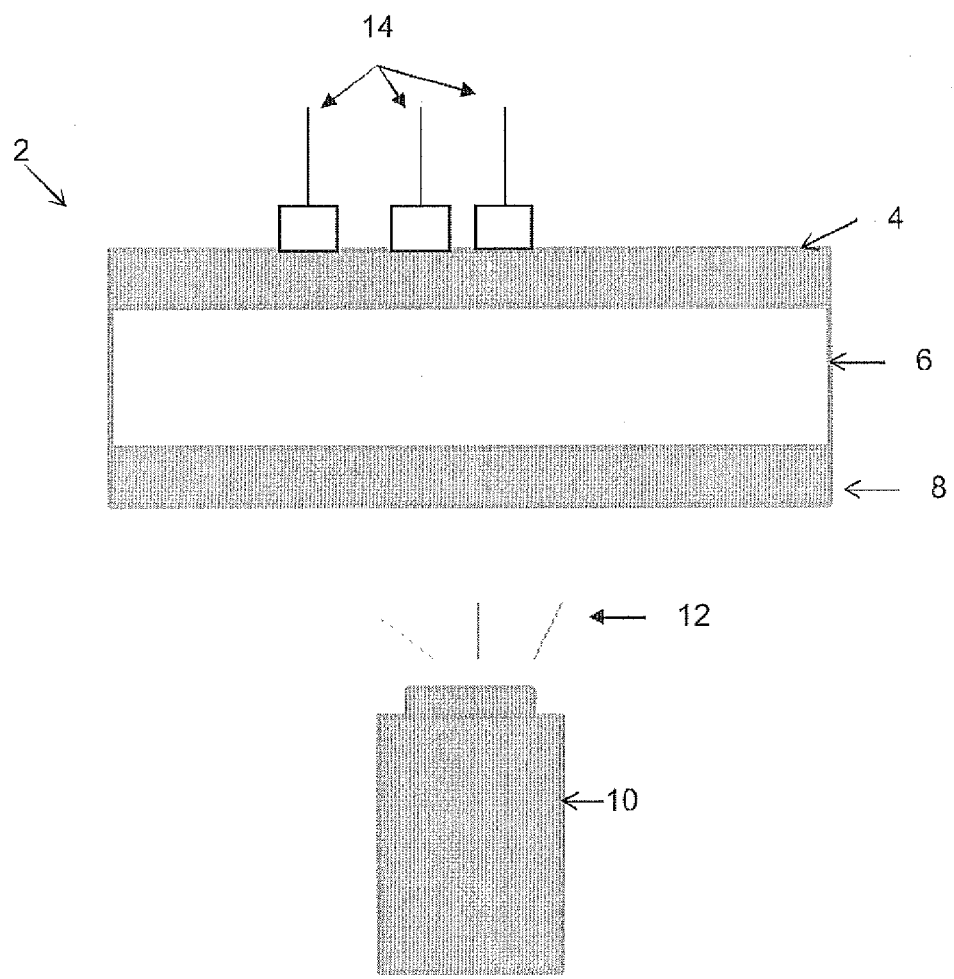
FIG. 1 is a schematic diagram illustrating a general overview of the invention.

FIG. 1 is a schematic diagram illustrating a general embodiment of the inventive near-field surface plasmon detector (SPD) structure 2. The near-field surface SPD detector 2 structure includes a first electrode 4, a semiconductor structure 6 that is positioned between the first electrode 4 and a semitransparent electrode 8 used in detecting surface plasmons. The first electrode 4 can be positioned on or near the semiconductor structure 6. The first electrode 4 can include one or more electrical contacts 14 used to output electrical power under operation. The sensor 2 generates power from the plasmon it does not actually require power. The one or more contacts 14 are formed on using standard techniques. Also, the first electrode 4 can include conductive materials, such as metals Ag or Au. The semiconductor structure 6 can include Si or other material structures comprising GaAs, or InP, such as AlGaAs, or InGaAsP. The semiconductor structure 6 can also include organic semiconductor arrangements as well for detecting surface plasmons. Moreover, the semiconductor structure 6 can also include a stack of various semiconductor layers.

A laser or light emitting source 10 is positioned below the semitransparent electrode 8. The electrode 8 is designed to allow light 12 from the laser or light emitting source 10 to pass the electrode 8 to be received by the semiconductor structure 6. The electrode 8 can include transparent materials, such as gold or silver. Also, the laser or light emitting source 10 can be positioned so emitted light 12 can be emitted at an off-angle when it arrives on the surface of the transparent electrode. In one implementation, the detector 2 forms a thin film organic heterojunction diode that converts the evanescent field of a surface plasmon at an aqueous-gold interface into photocurrents.

Figure 2A:
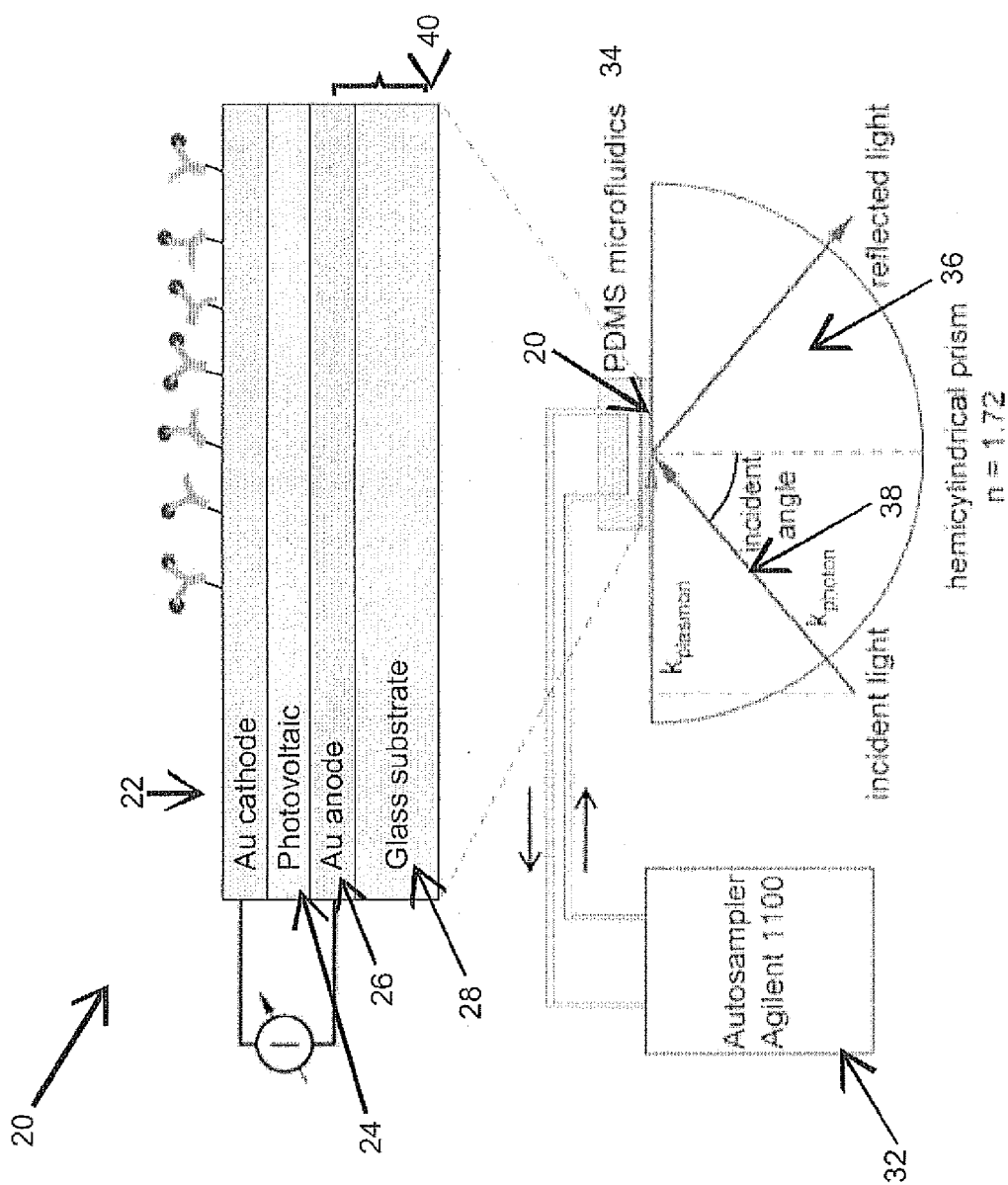
FIG. 2A is a schematic diagram of an embodiment of the invention.

FIG. 2A shows an embodiment of inventive near-field surface plasmon detector (SPD) structure 20. The near-field SPD structure 20 includes a thin layer of a semiconductor structure 24 sandwiched between a thin electrode 22, comprising a top Au electrode or the like, and an electrode 24, in this case a second Au layer. The top gold electrode 22 is circular with a radius of 1 mm. The top gold electrode 22 defines the area of the detector 20 and acts as the analyte binding surface. Biological materials are supplied by an autosampler 32 through a microfluidic circuit 34.

A p-polarized beam 38 from a 1 mW laser at $\lambda$=670 nm is aligned with the detector 20. The incident angle of the beam is adjusted by rotating a hemi-cylindrical prism 36 with the detector 20. The reflected light and device photocurrent are monitored as a function of the incident angle and binding events on the top gold layer 22. However, other light emitting sources such as VCELS or LEDs in conjunction with optical polarizers can be used to form a p-polarized beam.

Figure 2B:
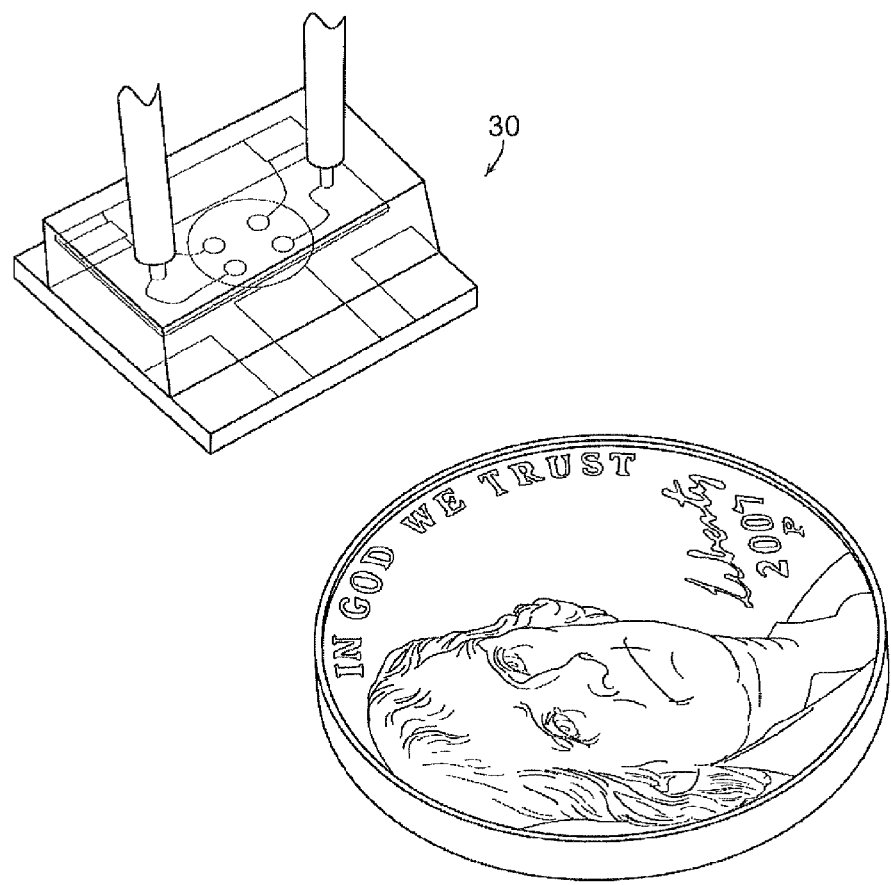
FIG. 2B is a photograph illustrating the invention

FIG. 2B is a photograph of the inventive device 30 integrated with a PDMS microfluidic chamber and connecting tubing. A US 5 cent coin is also shown to illustrate the scale of the inventive detector.

Conventional SPR sensors can consist of a gold film deposited on glass and immersed in water. The system is optically excited through the glass by a pump laser. When the angle of the laser beam 38 incident on the Au/water interface hits the resonance, surface plasmons are generated at the Au/water interface and the reflected light drops markedly. The resonant angle is a sensitive function of the refractive index of all media within the range of the surface plasmon, typically ~50 nm in Au and ~200 nm in water. Thus, analyte binding events at the Au/water interface modify the coupling of light into the surface plasmon and are detected from variations in the optical reflectivity.

The invention replaces the far field measurement of reflected tight with a direct near field measurement of the surface plasmons themselves. The sensitivity of conventional SPR sensors is maximized using a semitransparent electrode structure 40 having approximately a 50-nm-thick layer 26 of Au deposited on a glass substrate 28. But the electromagnetic field is negligible at the semiconductor structure 24 having a 50-nm-thick Au layer 22, preventing near field detection of the surface plasmons below the Au. Thus, to efficiently detect surface plasmons at the aqueous interface with minimal change in sensitivity, the semiconductor structure 24 is inserted between two Au layers (22 and 24); as shown in FIG. 2A.

The near field detector 20 is used to replace the conventional far field optical detector. It is integrated directly with an Au/water interface that supports surface plasmons and acts as the binding site for bio-analytes. The integration of the optical detector is arguably the key challenge confronting the integration of a SPR biosensor. The remaining optical element, the optical pump 36, can be replaced by a microcavity light emitting diode (LED), vertical cavity surface emitting laser (VCSEL) or any other light emitting device, placed under the near field detector and tuned for the wavevector of the plasmon resonance. Integration with an LED or VCSEL is possible with the invention as well as using an external laser.

The SPR sensors can be fabricated using thermal evaporation under vacuum (~$10^{-6}$ Torr). First, a 20-nm-thick gold anode with a 3-nm-thick chrome adhesion layer was deposited through a shadow mask onto a flint glass substrate 28, such as SF10 glass, with a refractive index n=1.72. The near-field semiconductor structure 24 can include organic photovoltaic materials CuPC, BCP, $C_{60}$, and PTCBI after thermal gradient purification. Note other materials system such InP or GaAs can be used in forming a near-field semiconductor structure 24. The 20-nm-thick top gold contact 22 was patterned using a shadow mask. The semiconductor structure 24 is approximately 0.79 $mm^2$.

After fabrication, the photovoltaic cells can optically be coupled using an index matching fluid to a hemi-cylindrical prism 36 made from the same material as the glass substrate 28, such as SF10 glass. The prism 36 was mounted on a translation stage above a motorized rotation stage aligned so that the motional rotation axis coincides with the symmetry axis of the cylindrical prism 36. The active region of the sample 40 was placed on the prism axis and a $\lambda$=670 nm laser beam 38 was collimated, p-polarized and focused on the same active region. The incident angle of the incoming laser beam 38 was varied by rotating the prism 36. The angular dependence of the photocurrent and the reflectivity as monitored by a silicon photo-detector, were measured with a Keithley 2602 dual source-meter. When using a LED or VCSEL in place of the prism 36, one can position the LED or VCSEL to produce off-angled light to be received by the detector 20. Alternatively, the near field detector can be fabricated on or positioned above an LED or VCSEL, where the LED or VCSEL comprises a resonant cavities consisting of semiconductor materials between two mirrors. For example, the thickness of the semiconductor materials and the period of a distributed feedback Bragg reflector mirror can be tuned to generate off-angle light propagating at incident angles>0 in FIG. 2A.

To determine the ideal properties of the semiconductor materials, one can calculate the sensitivity of a model near field SPR detector. The top 22 and bottom gold layers 26 are 20-nm-thick. The top surface 22 of the device 20 is immersed in buffer with a refractive index n=1.38. The substrate 28 is glass with a refractive index n=1.72. The Poynting vector within the model device is calculated using a transfer matrix method assuming plane wave incident light. To detect the surface plasmon in the near field the semiconductor must exhibit strong optical absorption. One can assume that the semiconductor is 50-nm-thick with an extinction coefficient k=0.2. The sensitivity of the detector is calculated from the relative change hi absorption within the semiconductor given the introduction of an interfacial 5-nm-thick protein layer with refractive index n=1.40.

Figures 3A, 3B:
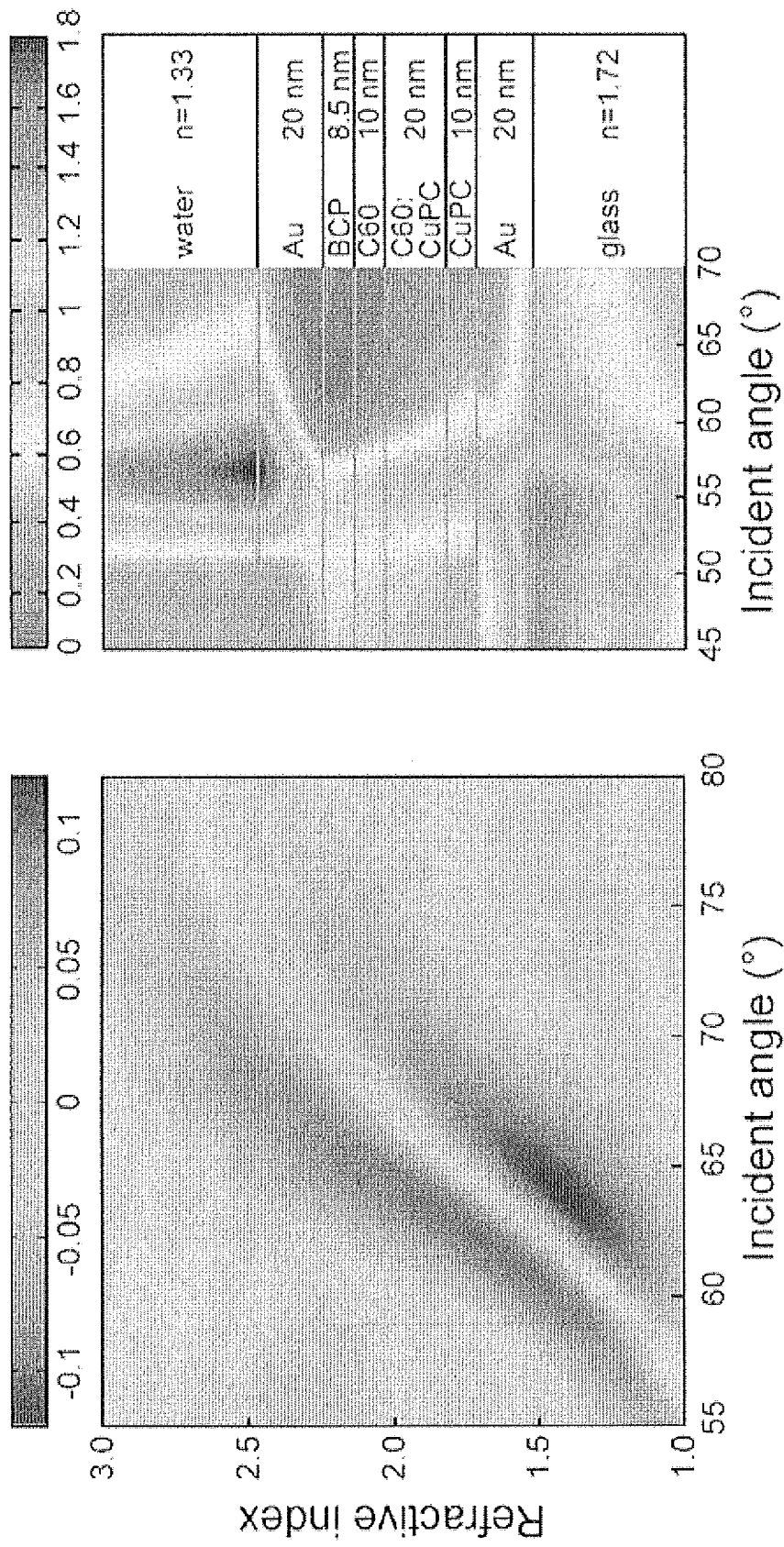
FIG. 3A is a simulation of the sensitivity of a near field surface plasmon detector as a function of the refractive index of the semiconductor material.
FIG. 3B is simulation illustrating the structure of the near field surface plasmon detector and amplitude of the electric field for the transverse magnetic mode within the device.

As shown in FIG. 3A, one can find that the sensitivity of the model device is maximized for semiconductor refractive indices between n=1.3 and n=1.8. The relative change in absorption within the semiconductor is 30% for the optimal choice of refractive index. When combined with the requirement for strong optical absorption, this calculation supports the choice of organic semiconductors for this application. For example, the archetype organic photovoltaic material copper phthalocyanine (CuPC) exhibits n=1.7 and k=0.2 at $\lambda$=650 nm.

To compare the sensitivity of the near field detector to that of a conventional SPR, one can also calculate the relative change in reflection from a 50-nm-thick Au layer. The same 5-nm-thick protein later with refractive index n=1.40 causes a 60% change in reflection, suggesting that the near field detector should exhibit roughly half the sensitivity of a conventional device. The calculated sensitivity of the near field detector should not be considered as a limit, however, since its structure contains opportunities for design optimization. For example, the bottom Au contact can be replaced by a lower loss Ag electrode.

Consistent with the refractive index guidelines of FIG. 3A, a practical organic semiconductor-based photovoltaic detector is designed. The anode is a 20-nm-thick gold layer. The donor material within the organic photovoltaic is a 10-nm-thick film of CuPC. The acceptor material is a 10-nm-thick film of buckminsterfullerene ($C_{60}$). To increase optical absorption, a 20-nm-thick bulk heterostructure consisting of a 1:1 mixture of the donor and acceptor materials is deposited between the donor and acceptor layers. The cathode includes an 8.5-nm-thick layer of bathocuproine (BCP) and a 20-nm-thick top gold layer.

The electric field within the CuPC/$C_{60}$ device is simulated in FIG. 3B as a function of the incident angle of optical excitation. Off resonance, the incident light is primarily reflected. But at the resonance, the incident light excites a surface plasmon that propagates in the plane of the Au and organic layers, significantly decreasing the reflected light and enhancing optical absorption within the photovoltaic. This enhancement in absorption is apparent in the strong electric field throughout the organic layers at the resonance condition.

Figure 4:
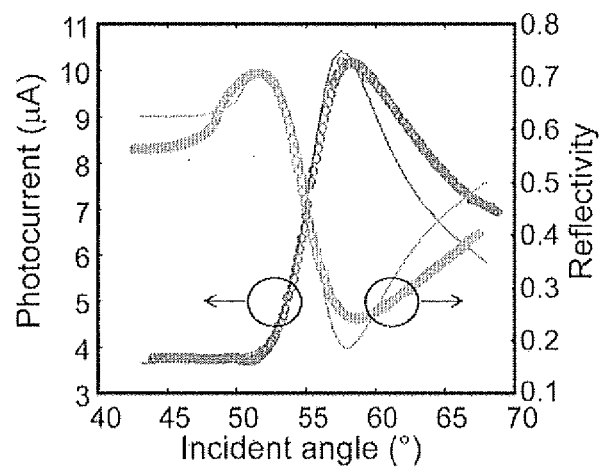
FIG. 4 is a graph illustrating the angular dependence of the photocurrent from the device and reflectivity.

The dependence of the photocurrent and reflectivity on the angle of incidence of the incoming light is measured and compared with the simulation in FIG. 4. Devices are immersed in a saline buffer typical of biosensing applications and exposed to a 1 mW laser at $\lambda$=670 nm. Both data and simulations show an increase in photocurrent and a decrease in reflected light at the resonance condition (approximately 58°). The photocurrent at the surface plasmon resonance is approximately two times higher than the off resonance baseline due to enhanced absorption.

One can conclude that the reflectivity and photocurrent are equivalent measures of surface plasmon generation. However, the resonance width for the experimental plots exceeds the theoretical prediction, slightly lowering the sensitivity. The discrepancy is likely due to the 10 nm surface roughness of the Au layers within the device. Surface roughness lowers sensitivity by enhancing scattering of the surface plasmons, which decreases their lifetime and hence increases the angular width of the resonance. The scattering losses could be alleviated by careful preparation of the Au surfaces.

Figure 5:
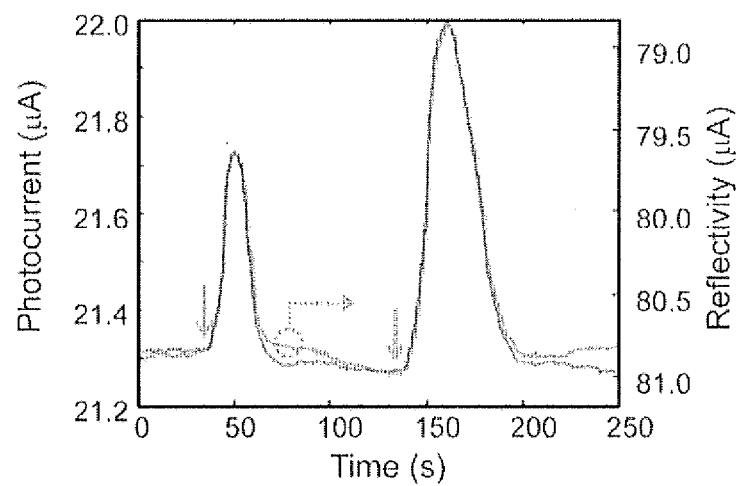
FIG. 5 is a graph illustrating sensor exposure to two water pulses in HEPES buffer flow.

Next, the sensor response is examined within a microfluidic system. To test the stability, sensitivity and reversibility of the sensor, water pulses of 30 and 60 s in length are injected into a constant flow of HEPES buffer. As shown in FIG. 5, the slight change of refractive index during the water pulses is detected by the sensor. One can observe a simultaneous change in reflectivity and current with proportional amplitude of the two quantities. The sensor shows reversibility at the end of the water pulse and good stability with negligible drift of the baseline. The water pulse response was tested for several incidence angles for the incoming light to find the maximal sensitivity angular coordinate for later binding assays.

Next, a specific binding assay for biotin-neutravidin is performed, an archetypal evaluation of sensing platforms. The surface of the sensor was first immersed in water for 2-3 hours with a 5:1 molar mixture of PEG (polyethylene glycol) acid disulfide and biotin PEG disulfide. The purpose of the functionalization is to space out the biotin moieties to avoid steric hindrance and spatial overlap between neutravidin binding sites. The PEG backbone prevents protein absorption on Au, minimizing non specific interaction with the surface. Normally, this functionalization is performed in ethanol because functionalization in water decreases the surface coverage due to the hydration volume around the ethylene glycol moieties.

The removal of water from the polyethylene glycol chains is thermodynamically unfavorable, and it prevents close packing of the polymer as well as surface access to protein species present in solution. But the water-based assembly is necessary here because the organic photovoltaic materials are weakly soluble in ethanol. Higher sensitivity could be obtained for surface functionalization with carboxyl methyl dextran hydrogel, which contains more binding sites for neutravidin within the range of the surface plasmon.

Figure 6:
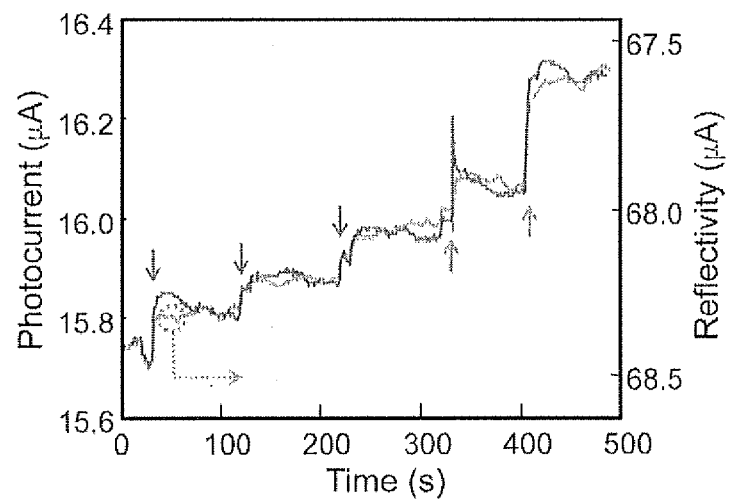
FIG. 6 is a graph illustrating the sensor response to casein and neutravidin.

For selective detection of neutravidin, any remaining non specific binding sites on the Au surface were passivated with a 1 mg/ml solution of casein. Then, in a constant flow of 250 µl/min HEPES buffer, the sensor was exposed to sequential pulses of 250 µg/ml neutravidin of 125 µl injection volume each. FIG. 6 shows a simultaneous response in the reflectivity and short circuit current when casein and neutravidin bind irreversibly to the functionalized surface of the sensor. The sensitivity of the near field device is 4 µg/cm$^2$. The same binding experiment using a conventional reflectivity-based detection of surface plasmons is performed on a 50-nm-thick gold layer, except that the surface functionalization was performed in ethanol.

A sensitivity from the conventional approach is obtained that is approximately three times better than the near field detector. From the theoretical analysis accompanying FIG. 2 a factor of two difference in sensitivity is expected. The additional loss in the near field detector is likely due to inferior surface functionalization because of the restriction to water rather than ethanol. Nevertheless, the relative similarity in sensitivities suggests that near field detection can be employed in the majority of applications for surface plasmon resonance detectors.

The stability of near field surface plasmon detectors is considered. Illumination is typically applied to contemporary biosensor chips for no longer than a few hours[8]. Thus, we expect that the stability of organic photovoltaic cells is sufficient for application in solid-state SPR detectors. The shelf life must be much longer than the operation life, but encapsulated organic photovoltaic cells have exhibited shelf lives exceeding 6000 hours.

The inventive devices are not encapsulated and are tested within 24 hours of surface functionalization. Stable photocurrent is observed throughout the 6 hour duration of the experiments with the top gold layer immersed in a saline buffer. Submerging the sensor in saline buffer solutions does not affect the electrical performance. In all cases the gold contact where the binding takes place was grounded. Diode characteristics in either air or buffer remained unchanged for anode bias in the −1V to +1V region, indicating that there are no leakage currents in solution.

Although stability problems are not observed in the experiments, $C_{60}$ is known to exhibit photo-induced degradation in the presence of oxygen. Consequently, one can also experiment with another acceptor, 3,4,9,10-perylene tetracarboxylic bisbenzimidazole (PTCBI). The combination of PTCBI and CuPC forms extremely stable photovoltaic devices. One can observe similar device performance from PTCBI/CuPC, however, the use of PTCBI significantly increased the density of short circuit defects in these relatively thin devices.

Conventional SPR detectors measure the optical reflection in the far field. The invention replaces the far field detector with a near-field detector positioned below the electrode or Au binding surface. The correlation between far field reflectivity and photocurrent from the near field detector are observed in FIGS. 3-6 that demonstrates that the near field detectors can replace the traditional far field approach. One can observe a factor of three decrease in the sensitivity of the inventive near field detector compared to a conventional SPR detector.

The inventive near and far field approaches yields comparable sensitivity upon binding of biological species on the surface. Other possibilities for improving the sensitivity include using longer wavelength light, the selective replacement of Au by Ag, and reductions in surface roughness of the metal layers. When combined with a microcavity LED or VCSEL, the near field detector should allow the integration of SPR biosensors into thin film devices, improving portability and environmental stability, potentially lowering costs, and introducing a new approach to the unsolved problems of biosensing.

Although the present invention has been shown and described with respect to several preferred embodiments thereof, various changes, omissions and additions to the form and detail thereof, may be made therein, without departing from the spirit and scope of the invention.

What is claimed is:

1. A near-field surface plasmon detector comprising:
   a semiconductor structure that measures one or more surface plasmons of a sample being tested using incoming light being emitted from a light emitting source, the light emitting source is positioned so the light is emitted at an off angle; and
   a plurality of electrodes positioned on or near said semiconductor structure, said one of the electrodes comprises one or more electrical contacts used to output electrical power under operation, the one or more surface plasmons being used to provide power to the near-field plasmon detector, the semiconductor structure being sandwiched between the electrodes, wherein the arrangement of the semiconductor structure and the electrodes is a heterojunction diode that converts the evanescent field of the one or more surface plasmons at a liquid aqueous-gold interface into photocurrents.

2. The near-field surface plasmon detector of claim 1, wherein said light emitting source comprises a laser.

3. The near-field surface plasmon detector of claim 1, wherein said light emitting source comprises a LED or VCSEL.

4. The near-field surface plasmon detector of claim 1 further comprising a semitransparent electrode structure having one or more transparent materials, said semitransparent electrode structure receives said incoming light signal from said light emitting source.

5. The near-field surface plasmon detector of claim 4, wherein said semitransparent electrode structure comprises a glass substrate and an Au layer formed on said glass substrate.

6. The near-field surface plasmon detector of claim 1, wherein said semiconductor structure comprises organic materials.

7. The near-field surface plasmon detector of claim 1, wherein said semiconductor layer comprises Si or material structures comprising GaAs or InP.

8. The near-field surface plasmon detector of claim 1, wherein said semiconductor layer, and said one or more electrodes form a heterojunction diode.

9. The near-field surface plasmon detector of claim 1, wherein said one or more electrodes comprise Au or Ag.

10. The near-field surface plasmon detector of claim 1, wherein said semiconductor structure and said electrodes comprises a photovoltaic structure.

11. The near-field surface plasmon detector of claim 1, wherein said semiconductor layer comprises a stack having a plurality of semiconductor layers.

12. A method of performing a near-field surface plasmon detection comprising:
    providing a semiconductor structure that measures one or more surface plasmons of a sample being tested using incoming light being emitted from a light emitting source, the light emitting source being positioned so the light is emitted at an off angle; and
    positioning a plurality of electrodes on or near said semiconductor structure, said one or more electrode comprise one or more electrical contacts used to output electrical power under operation, the one or more surface plasmons being used to provide power to the near-field plasmon detector, the semiconductor structure being sandwiched between the electrodes, wherein the arrangement of the semiconductor structure and the electrodes is a heterojunction diode that converts the evanescent field of the one or more surface plasmons at a liquid aqueous-gold interface into photocurrents.

13. The method of claim 12, wherein said light emitting source comprises a laser.

14. The method of claim 12, wherein said light emitting source comprises a LED or VCSEL.

15. The method of claim 12 further comprising a semitransparent electrode structure having one or more transparent materials, said semitransparent electrode structure receives said incoming light signal from said light emitting source.

16. The method of claim 15, wherein said semitransparent electrode structure comprises a glass substrate and an Au layer formed on said glass substrate.

17. The method of claim 12, wherein said semiconductor structure comprises organic materials.

18. The method of claim 12, wherein said semiconductor layer comprises Si or material structures comprising GaAs or InP.

19. The method of claim 12, wherein said semiconductor layer, and said one or more electrodes form a heterojunction diode.

20. The method of claim 12, wherein said one or more electrodes comprise Au or Ag.

21. The method of claim 12, wherein said semiconductor structure and said electrodes comprises a photovoltaic structure.

22. The method of claim 12, wherein said semiconductor layer comprises a stack having a plurality of semiconductor layers.

* * * * *